United States Patent [19]

Lowell

[11] Patent Number: 4,556,579

[45] Date of Patent: Dec. 3, 1985

[54] METHOD FOR DEVELOPING AND FIXING LATENT FINGERPRINTS

[76] Inventor: Freeman H. Lowell, 510 24th St., West Palm Beach, Fla. 33407

[21] Appl. No.: 575,155

[22] Filed: Jan. 30, 1984

[51] Int. Cl.$^4$ .............................................. A61B 5/10
[52] U.S. Cl. ...................................... 427/1; 118/31.5; 118/715; 427/145; 427/255.4
[58] Field of Search ..................... 427/1, 255.4, 145; 118/715, 31.5

[56] References Cited

U.S. PATENT DOCUMENTS 2,938,292  5/1960  Jaskowsky et al. ..................... 427/1
4,407,842 10/1983  Shepard .................................. 427/1
4,461,235  7/1984  Morton .................................. 427/1

*Primary Examiner*—Norman Morgenstern
*Assistant Examiner*—Janyce A. Bell
*Attorney, Agent, or Firm*—Dressler, Goldsmith, Shore, Sutker & Milnamow, Ltd.

[57] ABSTRACT

A method and kit for developing and fixing latent fingerprints on a solid surface is disclosed. The object to be examined for latent fingerprints exposed to fumes which contact the object to develop and fix any latent fingerprints on the surface of the object. The fumes are generated by depositing liquid cyanoacrylate monomer onto a shaped, self-supporting fiber plug constituted by cellulose acetate fibers and a glycerol ester-type plasticizer.

10 Claims, No Drawings

METHOD FOR DEVELOPING AND FIXING LATENT FINGERPRINTS

TECHNICAL FIELD

The present invention relates to a method of developing and fixing latent fingerprints. More particularly, the present invention relates to an improved method of developing and fixing latent fingerprints utilizing a special, shaped, self-supporting fiber plug and cyanoacrylate deposited thereon so as to generate fumes or vapors which, upon contact with an object, develop and fix any latent fingerprints thereon.

Fingerprints are impressions of the system of ridges on the finger surface. Most latent fingerprints, i.e., those hidden from the unaided eye, are formed when perspiration escapes through the ridged surface. Human perspiration is a mixture of many substances including fatty acids, amino acids, salt, water, riboflavin, organic urea, potassium chloride and other substances.

The most commonly used technique for developing latent fingerprints is the dusting method which involves covering a surface or object with fine powders such as ground carbon or pumice. Other methods for developing latent fingerprints include treating a surface with the chemical ninhydrin; however, this chemical is difficult to use and is highly explosive. Still other methods for developing latent fingerprints include the fuming of objects with iodine gas, and the dipping of objects in silver nitrate. These methods are relatively messy, the developed fingerprints fade quickly and surfaces of objects on which latent prints are sought may be damaged. Laser light can also be used to expose and outline fingerprints. However, it is inconvenient and expensive to use as it requires a relatively heavy argon ion laser unit.

U.S. Pat. No. 4,297,383 describes an apparatus and method for developing latent fingerprints on an object by fuming the object with cyanoacrylate vapors. The apparatus comprises a first chamber to contain the object and to close to form an air tight seal, a second chamber to contain a pool and vapors of cyanoacrylate, and a pump system. The method involves pumping the vapors from the second chamber into the first chamber to develop the latent fingerprints on the object.

Another process for developing latent fingerprints, as described in Science News, vol. 123, No. 19, p. 294 (May 7, 1983), involves the use of two different solutions containing cyanoacrylates which are applied to a gauze generator pad. Fumes are generated after the pad is treated with the cyanoacrylates and are attracted to the water and amino acid molecules in perspiration and, thereby, develop fingerprints. The resulting prints can be removed with a non-caustic solvent. This particular process is not very reliable, however.

The present method, on the other hand, obviates the shortcomings of previously known fingerprint development methods and provides a technique that is reliable and relatively easy to use.

SUMMARY OF THE INVENTION

The present invention contemplates a method for developing and fixing latent fingerprints on an object by depositing a liquid cyanoacrylate monomer onto a porous, shaped, self-supporting fiber plug constituted by cellulose acetate fibers and a glycerol ester-type plasticizer, and exposing the latent fingerprint to the vapors that are generated. This method develops and stabilizes or fixes latent fingerprints much faster, more reliably and more permanently than the existing fingerprint development methods.

The thus developed fingerprints can then be dusted and lifted as often as necessary. The prints may only be removed by means of a solvent.

Another aspect of the present invention contemplates a kit which comprises a supply of liquid cyanoacrylate monomer, a supply of fiber plugs onto which the monomer is deposited, and a supply of a solvent for the resulting polymerizate, e.g., a nitromethane based solvent, for removal of the developed fingerprint when desired to do so.

DETAILED DESCRIPTION OF THE INVENTION

The liquid monomeric, cyanoacrylate monomers useful for practicing the present invention are polymerizable esters of 2-cyanoacrylic acid and are represented by the formula

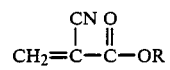

wherein R is an alkyl group having from one to four carbon atoms. The preferred cyanoacrylate monomer for the purposes of the present invention is methylcyanoacrylate. Such a monomer is commercially available from Three Bond of America, Inc., Torrence, Calif., under the trade name TB 1701. This monomer has a viscosity at 250° C. of 5 cps., a shear strength of 120 kg/cm, and a maximum setting time of 40 seconds. Other suitable cyanoacrylate monomers include those described in U.S. Pat. Nos. 3,523,628, 3,699,127, 3,742,018, 3,832,334, 3,836,377 and 4,038,345, the teachings of which are incorporated herein by reference.

The preferred self-supporting fiber plugs useful in practicing the present invention are porous, plasticizer-bonded filamentary tows shaped as a self-supporting plug. The manufacture of such plugs is described in U.S. Pat. Nos. 3,095,343, 3,111,702 and 3,313,665, the teachings of which are incorporated herein by reference. Plugs of this type are commercially available from American Filtrona Corporation, Richmond, Va.

These shaped, self-supporting plugs comprise at least about 50 percent by weight cellulose acetate fibers. If desired, minor amounts of other types of fibers such as cellulose, viscose, cotton, cellulose acetate-butyrate, cellulose propionate, and the like may also be present.

The porous plugs are treated with a glycerol ester-type plasticizer which serves to bond the filaments of the tow together and also promotes the cyanoacrylate monomer reaction that generates the fumes which expose and stabilize the latent fingerprints. Suitable glycerol ester-type plasticizers include the reaction products of glycerol with a saturated, monocarboxylic aliphatic acid containing one to four carbon atoms, inclusive, e.g., acetic acid, propionic acid, butyric acid. Illustrative of such plasticizers are glyceryl triacetate, glyceryl tripropionate, glyceryl tributyrate, and the like.

The plasticizer is usually present in an amount of about 5 to about 15 percent by weight of the fibers.

In operation, the method of the present invention comprises placing, in an enclosed area, at least one treated plug near an object to be examined for the presence of latent fingerprints on the surface of that object.

The size and/or number of plugs to be used in any given instance is dependent upon the surface area of the object to be examined.

The plug is then wetted with a liquid monomeric, polymerizable ester of 2-cyanoacrylic acid. The contact between the monomer and the treated cylinder creates vapors or fumes which contact the surface of the object to be examined. The fumes, in turn, react with fatty acids, amino acids, salts and other related oils present in perspiration which is left on objects after being handled by an individual and produce a permanent mark.

The resulting reaction forms a fingerprint which is stable and durable. The resulting developed and fixed latent fingerprint may be dusted, lifted and/or photographed as often as required without damage to the developed fingerprint. Depending upon the surface area and the temperature and humidity of the location of the object to be examined, the development and fixing of the latent fingerprint is accomplished in a relatively short time period. Under normal conditions, such as room temperature, and in an enclosed area in which the fuming is carried out, such development and stabilization or fixing of latent fingerprints may be accomplished in about thirty seconds to about five minutes.

Solid surfaces on which the present invention may be utilized include, but are not limited to, glass, plastic, wood, metal, rubber, paper, and the like.

The developed fingerprints may be removed from the surface of the object by a solvent for the resulting polymerizate. Nitroparaffin solvents such as nitromethane, nitroethane, 1-nitropropane, 2-nitropropane, and the like are preferred. Nitromethane and other nitromethane-based solvents are particularly preferred for this purpose. Typical other solvents suitable for this purpose are the nitrile ($C_1$ to $C_4$ alkyl cyanide) solvents such as acetonitrile, pivalonitrile and the like, ketone solvents such as acetone, and the like.

The present invention may be utilized, in virtually all cases, at the site of the object to be examined for latent fingerprints. This eliminates the time and expense of removing the object to a laboratory for examination. The developed fingerprints cannot be over- or under-processed and do not leave any residual dust once they are removed from the object by the solvent.

Another aspect of the present invention provides a kit for developing and fixing latent fingerprints on an object that is faster, more efficient and more economical than any method or kit heretofore known. This kit contains a supply of the liquid cyanoacrylate monomer, a supply of shaped, self-supporting fiber plugs, and a supply of a solvent for the resulting cyanoacrylate monomer-derived polymerizate, e.g., a nitroparaffin solvent, or the like as discussed above.

The foregoing is intended as illustrative of the present invention but not limiting. Numerous variations and modifications may be effected without departing from the true spirit and scope of the invention.

What is claimed is:

1. A method for developing and fixing latent fingerprints on a solid surface which comprises the steps of:
   (a) providing a porous, shaped, self-supporting plug constituted by cellulose acetate fibers and a glycerol ester-type plasticizer;
   (b) depositing a liquid cyanoacrylate monomer onto the plug in an amount sufficient to generate fumes; and
   (c) exposing a solid surface suspected of bearing a latent fingerprint to the generated fumes for a period of time sufficient to develop such latent fingerprint.

2. The method in accordance with claim 1 wherein the provided plug is constituted by cellulose acetate fibers and glyceryl triacetate as the plasticizer.

3. The method in accordance with claim 1 wherein the glycerol ester-type plasticizer is a reaction product of glycerol with a saturated monocarboxylic aliphatic acid containing one to four carbon atoms, inclusive.

4. The method in accordance with claim 1 wherein the deposited liquid cyanoacrylate monomer can be represented by the formula $$CH_2=\underset{\underset{CN}{|}}{C}-\underset{\underset{O}{\|}}{C}-OR$$

wherein R is an alkyl group having from one to four carbon atoms.

5. The method in accordance with claim 1 wherein the deposited liquid cyanoacrylate monomer is methylcyanoacrylate.

6. A fingerprint developing kit comprising a supply of liquid cyanoacrylate monomer, a supply of shaped, self-supporting fiber plugs constituted by cellulose acetate fibers and a glycerol ester-type plasticizer; and a solvent for cyanoacrylate-derived polymerizate.

7. The fingerprint developing kit of claim 6 wherein said cyanoacrylate monomer is methylcyanoacrylate.

8. The fingerprint developing kit of claim 6 wherein said plugs contain glyceryl triacetate as the plasticizer.

9. The fingerprint developing kit of claim 6 wherein said solvent is a nitroparaffin.

10. The fingerprint developing kit of claim 9 wherein said solvent is nitromethane.

* * * * *